US00PP13988P29

(12) United States Plant Patent
Hanes

(10) Patent No.: US PP13,988 P2
(45) Date of Patent: Jul. 15, 2003

(54) VERBENA PLANT NAMED 'ESCA BURG TWO'

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/092,620

(22) Filed: Mar. 8, 2002

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Annette H. Para
(74) *Attorney, Agent, or Firm*—Jondle & Associates PC

(57) ABSTRACT

A verbena cultivar particularly distinguished by purple colored flowers, vigorous growth and low trailing habit.

1 Drawing Sheet

GENUS AND SPECIES

Verbena hybrida.

VARIETY DENOMINATION

'Esca Burg Two'.

BACKGROUND OF THE NEW PLANT

The present invention comprises a new and distinct cultivar of verbena, botanically known as Verbena hybrida, and hereinafter referred to by the cultivar name 'Esca Burg Two'. The new cultivar is asexually reproduced from vegetative cuttings and tissue culture resulting from the cross of the seed/pod parent 98-683-2, a red proprietary line that is unnamed and unpatented×Temari Burgundy (PPAF), a purple commercial line.

'Esca Burg Two' is a product of a planned breeding program intended to create new verbena cultivars with burgundy colored flowers, dark green foliage, vigorous growth and low trailing habit.

The new cultivar was created in 2000 in Gilroy, Calif. and has been asexually reproduced repeatedly by vegetative cuttings and tissue culture in Gilroy, Calif. over a one and a half year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new verbena plant is illustrated by the accompanying photograph which shows blooms, buds, and foliage of the plant in full color, the colors shown being as true as can be reasonably obtained by conventional photographic procedures.

The drawing shows overall plant habit and the mature inflorescence.

DESCRIPTION OF THE NEW CULTIVAR

The following detailed descriptions set forth the distinctive characteristics of 'Esca Burg Two'. The data which defines these characteristics were collected from asexual reproductions carried out in Gilroy, Calif. The plant history was taken on 15 week old plants grown in one gallon pots, in a double polygreenhouse under natural light and color readings were taken in the greenhouse. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Verbena hybrida.
*Commercial.*—Verbena.
Form: Low trailing annual, decumbent.
Growth and branching habit: Vigorous growing, moderate basal branching; low trailing habit.
Height: From soil level to top of blooms: Approximately 12–16 cm.
Width: Approximately 65–70 cm.
Time to produce a finished flowering plant: 10 weeks.
Outdoor plant performance: Typical bedding plant culture, full sun in the garden, hanging baskets or container plants.
Time to initiate roots: Approximately 4 days in the greenhouse.
Time to develop roots: Approximately 7 days in the greenhouse.
Root description: Fibrous, fleshy, white.

THE LEAVES

Length: 5.3–5.5 cm.
Width: 3.0–3.5 cm.
Leaf blade shape: Ovate.
Leaf margin: Irregular, crenately incised.
Apex aspect: Obtuse.
Base aspect: Cuneate.
Foliage color: Upper surface — Green RHS 137B; Lower surface is green RHS 137C.
Texture:
*Upper.*—Pilose.
*Lower.*—Heavy on midvein with some glandular hairs.
Venation: Pinnate.
Venation color: Green RHS 145C.
Petiole length: 0.7–1.2 cm.
Petiole diameter: 2.0 cm.
Petiole color: Green RHS 145C.

Petiole texture: Heavy pilose, short and long; glandular hairs with violet color.

THE STEM

Length: 30–55 cm.
Diameter: 0.4–0.5 cm.
Internode length: 3.9–4.2 cm.
Color: Yellow-green RHS 144A.
Texture: Heavy pilose (short and long), glandular hairs with violet color.
Stem anthocyanin: None.

THE BUD

Shape: Linear.
Diameter: 0.2–0.3 cm.
Length: 1.2–1.6 cm.
Color at tight bud: Greyed-purple RHS 187A.

THE FLOWER

Blooming habit: Continuous throughout the growing season.
Inflorescence type: Spike.
Spikes per plant: 50–60 in the greenhouse.
Spike diameter: Approximately 4.5–5.0 cm.
Spike depth: Approximately 1.7–2.5 cm.
Peduncle length: 8.0–10.0 cm.
Peduncle diameter: 0.3 cm.
Peduncle color: Yellow-green RHS 144A.
Peduncle texture: Pilose; glandular hairs with violet color (more than stems).
Flower color: Upper petal surface is red-purple RHS 59A but more velvety red-burgundy; Lower petal surface is red-purple RHS 59B.
Floret form: Salverform; sessile on spikes.
Floret (limb) diameter: Approximately 1.6–1.8 cm.
Corolla tube length: Approximately 1.9–2.1 cm.
Number florets per spike: 29–35 (closed to fully open florets).
Number of petals: Gamopetalous, five lobed.
Petal size:
*Length of one lobe.*—0.8 cm.
*Width of one lobe.*—0.8–0.9 cm.
Petal lobe shape: Obcordate.
Petal apex shape: Emarginate.
Petal base shape: Fused.
Petal margin: Entire.
Petal texture: Papillose; pilose on lower side.
Sepals: Five sepals whose margins are fused to each other along their length with a transparent membrane of less than 1 mm in width with one smaller sepal (7 mm) attached to the base of the calyx.
Calyx length: Approximately 0.5–0.6 cm.
Calyx width: Approximately 2.0 cm.
Calyx shape: Linear.
Calyx apex: Acuminate.
Calyx color: Yellow-green RHS 143B.
Calyx texture: Short pilose, many glandular hairs with and without violet color.
Lastingness of individual blooms: One week.
Fragrance: None

THE REPRODUCTIVE ORGANS

Stamens: Anthers and filaments fused to upper half of corolla tube; four anthers with two pollen sacs per anther.
Pollen amount and color: Slight, yellow RHS 1A.
Pistil: One style approximately 1.8 cm; recurved at the stigma.
Stigma color: Green RHS 143C.
Fruit seed set: Does not freely set seed but can produce 4 narrow nutlets, approximately 4 mm long; colored grey-brown RHS 199D and enclosed in the dried calyx.

DISEASE AND INSECT RESISTANCE

Tolerant to mildew.

COMPARISON WITH KNOWN CULTIVARS

When the instant plant is compared to the male parent 'Temari Burgundy' (PPAF) the 'Esca Burg Two' has leaves that are much larger than 'Temari Burgundy' (3.3 cm long× 2.5 cm wide). 'Esca Burg Two' flower color is more velvety burgundy than 'Temari Burgundy' which is more purple (RHS 71A).

When 'Esca Burg Two' is compared to the female parent 'Tort Red', 'Esca Burg Two' has burgundy colored flowers as compared to red for 'Tort Red'. 'Esca Burg Two' is a very vigorous trailing plant and 'Tort Red' is moderate with vigor and not trailing.

I claim:

1. A new and distinct cultivar of verbena plant as shown and described herein.

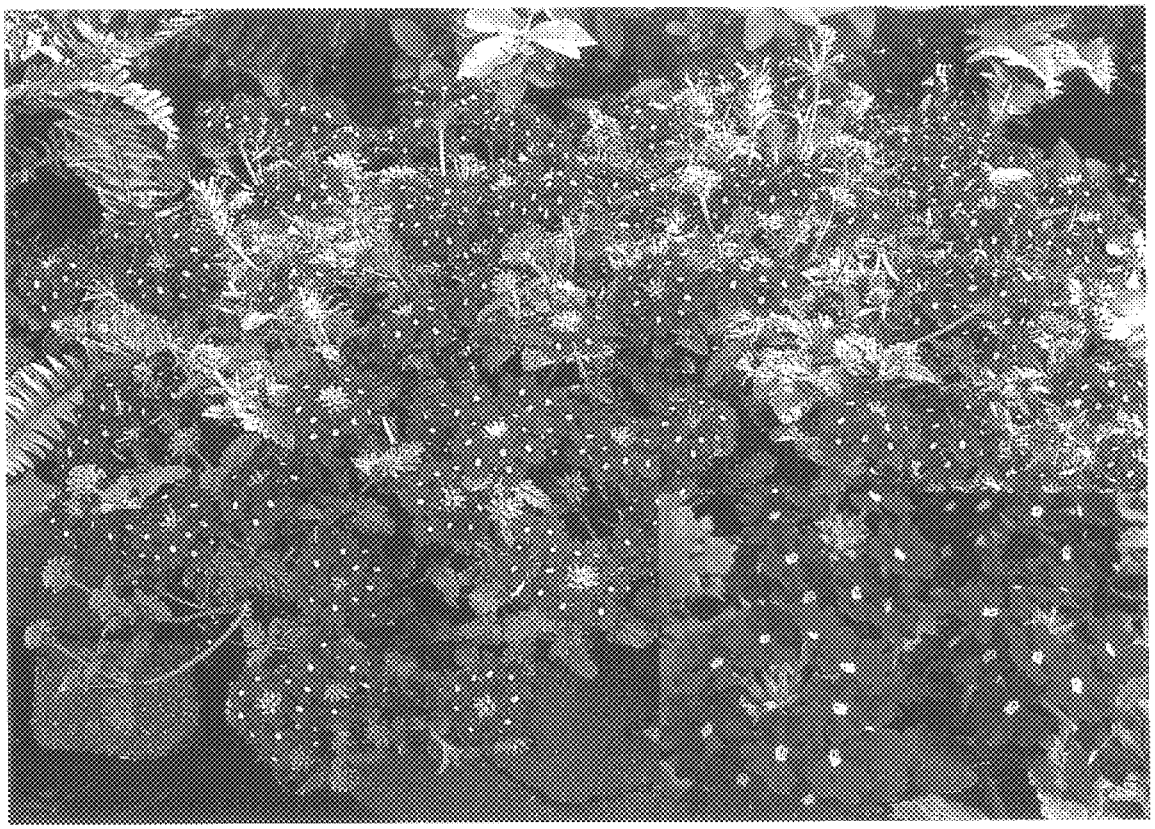

* * * * *